US012665070B2

(12) United States Patent
Galban et al.

(10) Patent No.: US 12,665,070 B2
(45) Date of Patent: Jun. 23, 2026

(54) DICTIONARY-BASED TISSUE ASSESSMENT AND ABNORMALITY DETECTION

(71) Applicant: The Regents of the University of Michigan, Ann Arbor, MI (US)

(72) Inventors: Craig Galban, Ann Arbor, MI (US); Sundaresh Ram, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 262 days.

(21) Appl. No.: 18/560,565

(22) PCT Filed: May 17, 2022

(86) PCT No.: PCT/US2022/029671
§ 371 (c)(1),
(2) Date: Nov. 13, 2023

(87) PCT Pub. No.: WO2022/245854
PCT Pub. Date: Nov. 24, 2022

(65) Prior Publication Data
US 2024/0274271 A1 Aug. 15, 2024

Related U.S. Application Data

(60) Provisional application No. 63/189,389, filed on May 17, 2021.

(51) Int. Cl.
*G16H 30/20* (2018.01)
*G16H 30/40* (2018.01)
(52) U.S. Cl.
CPC ............. *G16H 30/20* (2018.01); *G16H 30/40* (2018.01)

(58) Field of Classification Search
CPC ............................... G16H 30/20; G16H 30/40
See application file for complete search history.

(56) References Cited

U.S. PATENT DOCUMENTS

2014/0119628 A1* 5/2014 Elad ........................ G06T 12/20
382/131
2015/0024969 A1* 1/2015 Langley ............. G01N 33/6848
506/15

(Continued)

OTHER PUBLICATIONS

Li, Structured Sparse Subspace Clustering: A Joint affinity Learning and Subspace Clustering Framework, Oct. 2017 arXiv: 1610.05211 (Year: 2017).*

(Continued)

*Primary Examiner* — Wednel Cadeau
(74) *Attorney, Agent, or Firm* — Lempia Summerfield Katz LLC

(57) ABSTRACT
A computer-implemented method of tissue assessment includes obtaining a plurality of input data samples, each input data sample being representative of tissue in one of multiple views, determining a set of sparse codes for each input data sample of the plurality of input data samples, determining a reconstruction error for the set of sparse codes relative to each dictionary of a set of machine-learned composite dictionaries, and providing the tissue assessment in accordance with the machine-learned composite dictionary in the set of machine-learned composite dictionaries having a minimum reconstruction error of the determined reconstruction errors. Each machine-learned composite dictionary includes a plurality of constituent dictionaries, each constituent dictionary of the plurality of constituent dictionaries being associated with a respective one of the multiple views.

18 Claims, 8 Drawing Sheets

(56)                    References Cited

U.S. PATENT DOCUMENTS

2018/0068443 A1*  3/2018  Yin ......................... A61B 6/032
2018/0165809 A1*  6/2018  Stanitsas ................... G06T 5/40

OTHER PUBLICATIONS

Li et al., Structured Sparse Subspace Clustering: A Joint affinity Learning and Subspace Clustering Framework, Oct. 2017 arXiv; 1610.05211 (Year: 2017).*

S. Haykin, Neural Networks and Learning Machines, Upper Saddle River, NY, USA: Pearson, 2009.

V. Vapnik, The Nature of Statistical Learning Theory, Springer-Verlag, Berlin, Heidelberg, 1995.

A. Busacker et al., "A multivariate analysis of risk factors for the air-trapping asthmatic phenotype as measured by quantitative CT analysis" Chest, vol. 135, No. 1, pp. 48-56, Dec. 2009.

C.-P. Wei, Y.-W. Chao, Y.-R. Yeh, and Y.-C. F. Wang, "Locality-sensitive dictionary learning for sparse representation based classification"; Pattern Recognit., vol. 46, No. 5, pp. 1277-1287, May 2013.

Chun-Guang Li et al., Structured Sparse Subspace Clustering: A Joint Affinity Learning and Subspace Clustering Framework, IEEE Transactions on Image Processing; vol. 26; 2017; 14 pp.

G. Gonzalez et al., "Disease staging and prognosis in smokers using deep learning in chest computed tomography"; Am. J Respir. Crit. Care Med., vol. 197, No. 2, pp. 193-203, Jan. 2018.

I. Diamant et. at., "Task-driven dictionary learning based on mutual information for medical image classification," IEEE Trans. Biomed. Eng., vol. 64, No. 6, pp. 1380-1392, Jun. 2017.

International Preliminary Report on Patentability cited in corresponding international patent application No. PCT/US2022/029671; Nov. 21, 2023; 8 pp.

International Search Report and Written Opinion cited in corresponding international patent application No. PCT/US2022/029671; Sep. 27, 2022; 9 pp.

J. A. Tropp and A. C. Gilbert, "Signal recovery from random measurements via orthogonal matching pursuit"; IEEE Trans. Inf. Theory, vol. 53, No. 12, pp. 4655-4666, Dec. 2007.

J. Mairal, F. Bach, and J. Ponce, "Task-driven dictionary learning"; IEEE Trans. Pattern Anal. Mach. Intell., vol. 34, No. 4, pp. 791-804, Apr. 2012.

J. Mairal, "SPArse Modeling Software," Version 2.6, URL http://spams-devel.gforge.inria.fr/downloads.html; 2017; 104 pp.

J. Tan et al., "Texture-based segmentation and analysis of emphysema depicted on CT images" in Proc. Of SPIE Medical Imaging 2011: Biomedical Applications in Molecular, Structural, and Functional Imaging, 2011, vol. 7965, p. 79651V.

L. G. Estrella et al., "Computed tomography quantification of tracheal abnormalities in COPD and their influence on airflow limitation"; Med. Phys., vol. 44, No. 7, pp. 3594-3603, Jul. 2017.

M. Elad, M. A. Figueiredo, and Y. Ma, "On the role of sparse and redundant representations in image processing"; Proc. of IEEE, vol. 98, No. 6, pp. 972-982, Jun. 2010.

O. M. Mets et al., "Early identification of small airways disease on lung cancer screening CT: Comparison of current air trapping measures"; Lung, vol. 190, No. 6, pp. 629-633, Dec. 2012.

O. Solyanik et al., "Quantification of pathologic air trapping in lung transplant patients using CT density mapping: Comparison with other CT air trapping measures"; PLOS One, vol. 10, No. 10, pp. e0139102, Oct. 2015.

R. Karimi et al., "Differences in regional air trapping in current smokers with normal spirometry" Eur. Respir. J, vol. 49, No. 1, pp. 1600345, Jan. 2017.

R. S. J. Estepar et al., "Computed tomographic measures of pulmonary vascular morphology in smokers and their clinical implications," Am. J Respir. Crit. Care Med., vol. 188, No. 2, pp. 231-239, Jul. 2013.

S. Bahrampour, N. M. Nasrabadi, A. Ray, and W. K. Jenkins, "Multimodal task-driven dictionary learning for image classification"; IEEE Trans. Image Process., vol. 25, No. 1, pp. 24-38, Jan. 2016.

S. Matsuoka et al., "Quantitative CT assessment of chronic obstructive pulmonary disease"; Radiographics, vol. 30, No. 1, pp. 55-66, Jan. 2010.

S. Ram and J. J. Rodriguez, "Image super-resolution using graph regularized block sparse representation"; in Proc. of IEEE Southwest Symp. Image Anal. Interp. (SSIAI'16), 2016, pp. 69-72.

S. Ram and J. J. Rodriguez, "Single image super-resolution using dictionary-based local regression"; in Proc. of IEEE Southwest Symp. Image Anal. Interp. (SSIAI'14), 2014, pp. 121-124.

S. Ram and J. J. Rodriguez, "Size-invariant detection of cell nuclei in microscopy images"; IEEE Trans. Med. Imag., vol. 35, No. 7, pp. 1753-1764, Jul. 2016.

S. Ram et al., "Three-dimensional segmentation of the ex-vivo anterior lamina cribrosa from second-harmonic imaging microscopy"; IEEE Trans. Biomed. Eng., vol. 65, No. 7, pp. 1617-1629, Jul. 2018.

T. Huu Vu et al., "Histopathological image classification using discriminative feature-oriented dictionary learning" IEEE Trans. Med. Imag., vol. 35, No. 3, pp. 738-751, Mar. 2016.

T.-H. Chan et al., "PCANet: A simple deep learning baseline for image classification?"; IEEE Trans. Image Process., vol. 24, No. 12, pp. 5017-5032, Dec. 2015.

W. T. Miller, J. Chatzkel, and M. G. Hewitt, "Expiratory air trapping on thoracic computed tomography: A diagnostic subclassification"; Ann. Am. Thorac Soc., vol. 11, No. 6, pp. 874-881, Jul. 2014.

* cited by examiner

DICTIONARY-BASED TISSUE ASSESSMENT AND ABNORMALITY DETECTION

CROSS-REFERENCE TO RELATED APPLICATION

This U.S. National Phase application is based on International Application No. PCT/US2022/029671, filed May 17, 2022, which claims the benefit of U.S. provisional application entitled "Dictionary-Based Tissue Assessment and Abnormality Detection," filed May 17, 2021, and assigned Ser. No. 63/189,389, the entire disclosures of which is are hereby expressly incorporated by reference. Priority benefit of these earlier filed applications is hereby claimed.

BACKGROUND OF THE DISCLOSURE

Field of the Disclosure

The disclosure relates generally to dictionary-based classification.

Brief Description of Related Technology

In lung transplantation, approximately 70% of lungs are declined for transplant. Strict criteria have been established to select suitable donor lungs. For instance, the ideal lung donor is age less than 55 years with short or no smoking history. Lungs suitable for transplant also exhibit excellent blood gas parameters, and a clear chest radiograph. As donor lungs are extremely rare, options are increasingly explored to expand the donor pool, including the use of extended criteria donors, i.e., individuals who do not match the aforementioned ideal criteria. Unfortunately, techniques for screening the lungs of extended criteria donors have been limited.

Air trapping involves abnormal retention of inspired air during expiration. Air trapping is observed on a variety of obstructive lung diseases such as bronchiectatis, interstitial lung disease, chronic bronchitis, bronchiolitis olbiterans, cystic fibrosis, asthma, and small airways disease. Quantification and characterization of air trapping in expiratory computed tomography (CT) images have been shown to be useful for differential diagnosis, stratification, and risk prediction. Therefore, there is a significant interest in developing quantitative image analysis methods for air trapping classification in CT images as a complement to the effort of the radiologists in diagnosis process. Unfortunately, manual segmentation and classification of air trapping within expiratory CT images usually involves a large amount of time, especially for large-scale data processing. Manual segmentation and classification is also prone to multiple errors caused by background clutter, non-uniform illumination, imaging noise, and subjective bias.

The above-referenced and other challenges in lung tissue assessment have motivated the development of computerized frameworks for tissue classification and abnormality detection. Such frameworks attempt to classify expiratory CT images, thereby alleviating the workload on radiologists by sieving out obviously diseased and also healthy cases. The use of such frameworks allows the radiologists to spend additional time on more sophisticated cases. In the diagnosis process, the radiologists often look for visual cues, or features in CT images to categorize the regions within the images, e.g., as belonging to areas of air trapping or not. These features may involve distinguishable characteristics such as size, shape, and texture, or from spatially related structures. The features may also include the presence of particular regions at times. While various quantitative CT air trapping measurements have been proposed to recognize such features, air trapping and other image classification in CT remains a challenging problem.

Image sparsity has emerged as one of the most significant properties of natural images. Sparsity-based regularization has been used for various image processing applications. The applicability of sparsity-based methods has also been investigated for medical image classification. In image classification, the sparse model assumes that each patch within an image can be accurately represented by a few elements of a basis set called a dictionary, which can be learned from images. For an image classification problem, a separate class-specific dictionary is learnt from patches belonging to each class of images. During use, an incoming image patch is assigned to a class via a reconstruction error-based metric.

SUMMARY OF THE DISCLOSURE

In accordance with one aspect of the disclosure, a computer-implemented method of tissue assessment includes obtaining, with a processor, a plurality of input data samples, each input data sample being representative of tissue in one of multiple views, determining, with the processor, a set of sparse codes for each input data sample of the plurality of input data samples, determining, with the processor, a reconstruction error for the set of sparse codes relative to each dictionary of a set of machine-learned composite dictionaries, and providing, with the processor, the tissue assessment in accordance with the machine-learned composite dictionary in the set of machine-learned composite dictionaries having a minimum reconstruction error of the determined reconstruction errors. Each machine-learned composite dictionary of the set of machine-learned composite dictionaries includes a plurality of constituent dictionaries, each constituent dictionary of the plurality of constituent dictionaries being associated with a respective one of the multiple views.

In accordance with another aspect of the disclosure, a computer-implemented method for building a machine-learned classifier includes obtaining, with a processor, a plurality of training data samples, each training input sample being associated with one of a plurality of classes, and each input data sample being representative of tissue in one of multiple views, and implementing, with the processor, a sparse code-based optimization to build a set of composite dictionaries of the machine-learned classifier based on the plurality of data samples of the training data, each composite dictionary of the plurality of composite dictionaries being representative of one of the plurality of classes. Each composite dictionary of the set of composite dictionaries includes a plurality of constituent dictionaries, each constituent dictionary of the plurality of constituent dictionaries being associated with a respective one of the multiple views.

In accordance with yet another aspect of the disclosure, a computer-implemented method for building a machine-learned classifier includes obtaining, with a processor, a plurality of training data samples, each training input sample being associated with one of a plurality of classes, and implementing, with the processor, a sparse code-based optimization to build a set of dictionaries of the machine-learned classifier based on the plurality of data samples of the training data, each dictionary of the set of dictionaries being representative of one of the plurality of classes. Implementing the sparse code-based optimization includes iteratively updating bases of a respective dictionary of the set of dictionaries in accordance with a minimization problem, the minimization problem including a first component directed to minimizing differences of the training data samples associated with the class for which the respective dictionary is representative, and a second component directed to maximizing differences between the training data samples associated with a different class for which the respective dictionary is not representative.

In accordance with still another aspect of the disclosure, a system for tissue assessment includes a scanner configured to capture scan data representative of tissue in multiple views, a memory on which input instructions, sparse code optimization instructions, reconstruction error instructions, and output instructions are stored, a processor coupled to the memory and configured to execute the input instructions to generate a plurality of input data samples based on the scan data, and a storage device on which a set of machine-learned composite dictionaries is stored. The processor is configured to execute the sparse code optimization instructions to determine a set of sparse codes for each input data sample of the plurality of input data samples. The processor is configured to execute the reconstruction error instructions to determine a reconstruction error for the set of sparse codes relative to each machine-learned composite dictionary of the set of machine-learned composite dictionaries. The processor is configured to execute the output instructions to provide the tissue assessment in accordance with the machine-learned composite dictionary in the set of machine-learned composite dictionaries having a minimum reconstruction error of the determined reconstruction errors. Each machine-learned composite dictionary of the set of machine-learned composite dictionaries includes a plurality of constituent dictionaries, each constituent dictionary of the plurality of constituent dictionaries being associated with a respective one of the multiple views.

In connection with any one of the aforementioned aspects, the systems and/or methods described herein may alternatively or additionally include or involve any combination of one or more of the following aspects or features. Determining the set of sparse codes includes implementing, with the processor, an optimization based on each machine-learned composite dictionary of the set of machine-learned composite dictionaries. The optimization includes a joint I12 norm minimization calculation. The set of sparse codes are collectively representative of all of the multiple views. Obtaining the plurality of input data samples includes acquiring, with a scanner, three-dimensional image data of the tissue. The multiple views include respective cross-sectional views of the three-dimensional image data. Each constituent dictionary of the plurality of constituent dictionaries is associated with one of the respective cross-sectional views of the three-dimensional input image data. A first dictionary of the set of machine-learned composite dictionaries is representative of images of abnormal lung tissue. A second dictionary of the set of machine-learned composite dictionaries is representative of images of healthy lung tissue. The images of abnormal lung tissue are indicative of a presence of air-trapping. The images of healthy lung tissue are indicative of an absence of air-trapping. The computer-implemented method further includes implementing, by the processor, an image segmentation procedure on image data. The tissue assessment includes a prediction of therapeutic outcome. The prediction of therapeutic outcome is indicative of length of hospital stay. Implementing the sparse code-based optimization includes iteratively updating sparse codes for the plurality of training data samples. Implementing the sparse-code base optimization includes alternating between iteratively updating dictionary bases of a respective one of the set of composite dictionaries for a given set of the sparse codes and iteratively updating the sparse codes for a given set of the dictionary bases. Iteratively updating the sparse codes includes implementing an orthogonal matching pursuit (OMP) procedure. Implementing the sparse code-based optimization includes iteratively updating bases of a respective composite dictionary of the set of composite dictionaries in accordance with a minimization problem. The minimization problem includes a first component directed to minimizing differences of the training data samples associated with the class for which the respective composite dictionary is representative, and a second component directed to maximizing differences between the training data samples associated with a different class for which the respective composite dictionary is not representative. Iteratively updating the bases includes implementing a block coordinate descent procedure to update the bases one at a time. Implementing the sparse code-based optimization includes iteratively updating sparse codes for the plurality of training data samples. Implementing the sparse-code base optimization includes alternating between iteratively updating the bases for a given set of the sparse codes and iteratively updating the sparse codes for a given set of the bases. Iteratively updating the sparse codes includes implementing an orthogonal matching pursuit (OMP) procedure. Iteratively updating the bases includes implementing a block coordinate descent procedure to update the bases one at a time. Each training input data sample includes a training data patch, the training data patch including image data in one of multiple cross-sectional views. Each training data sample of the plurality of training data samples includes image data representative of a two-dimensional slice in one of multiple cross-sectional views. Each dictionary of the plurality of dictionaries includes a constituent dictionary for a respective cross-sectional view of the multiple cross-sectional views. The second component is scaled by a regularization parameter. The second component is subtracted from the first component.

BRIEF DESCRIPTION OF THE DRAWING FIGURES

For a more complete understanding of the disclosure, reference should be made to the following detailed description and accompanying drawing figures, in which like reference numerals identify like elements in the figures.

Figure 1:
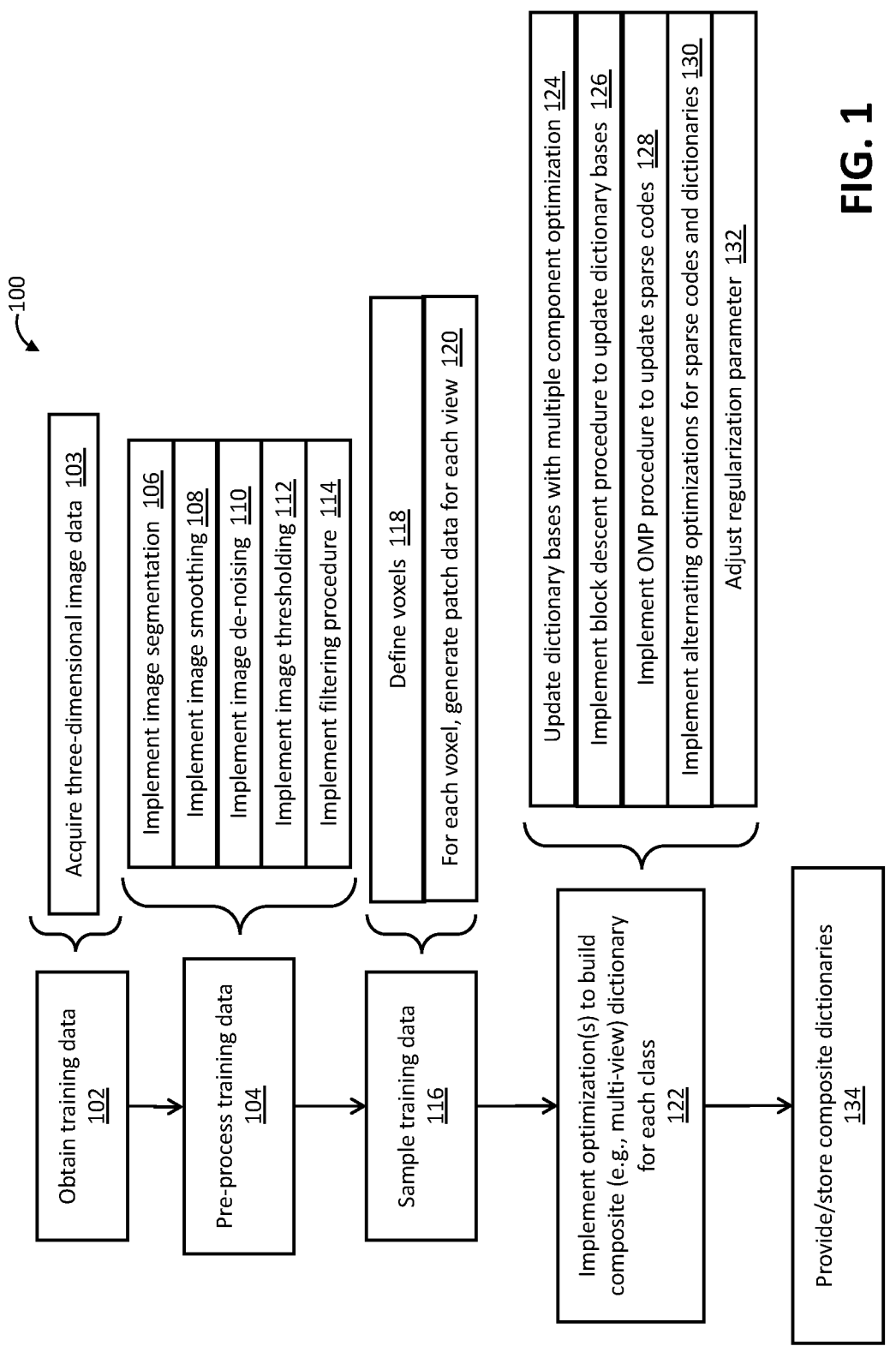
FIG. 1 is a flow diagram of a computer-implemented method for building a machine-learned classifier to build a plurality of machine-learned composite dictionaries in accordance with one example.

The embodiments of the disclosed systems and methods may assume various forms. Specific embodiments are illustrated in the drawing and hereafter described with the understanding that the disclosure is intended to be illustrative. The disclosure is not intended to limit the invention to the specific embodiments described and illustrated herein.

DETAILED DESCRIPTION OF THE DISCLOSURE

Methods and systems of tissue assessment and/or abnormality detection based on machine-learned composite dictionaries are described. Each composite dictionary used by the disclosed methods and systems includes a plurality of constituent dictionaries. Each constituent dictionary is associated with a respective dimension of a number of dimensions (e.g., views) of input data to be classified. Each class may thus be represented by a single dictionary despite involving data (e.g., dictionary bases) representative of, or otherwise associated with, different dimensions. The composite dictionaries may thus be considered to be multi-view dictionaries.

Methods for building a machine-learned classifier are also described. The disclosed methods of building may be task-driven. For instance, the disclosed methods of building implement a sparse code-based optimization to build the set of composite dictionaries. In some cases, the sparse code-based optimization involves iteratively updating a minimization problem that attempts to both minimize and maximize differences involving training data samples. The minimization problem is constructed such that, when building a respective dictionary for one of the classes, differences between training data samples associated with the class are minimized, and differences between other training data samples (associated with another class) are maximized.

The disclosed methods and systems are useful in various types of abnormality detection contexts. In some cases, the disclosed methods and systems are used for air trapping image classification. In other cases, the disclosed methods and systems are used for screening donor lungs. In these and other cases, the input data samples in such cases may be or otherwise include expiratory thoracic CT scan data of multiple views or dimensions.

Although described in connection with air trapping detection and donor lung classification, the disclosed methods and systems may be used for other types of classifications. For instance, the disclosed methods and systems may be used to detect a wide variety of abnormalities. Various types of tissue assessments may be provided. For instance, the disclosed methods and devices may be applied in contexts involving the assessment of other types of tissue. The nature of the assessment may vary accordingly. For instance, the disclosed methods and systems may be used to provide a prediction or other assessment involving tissue or other physiological functionality, including, for example, spirometric decline or the decline of pulmonary functionality more generally. Indeed, the disclosed methods and systems may be useful in connection with classification contexts not involving tissue. The nature of the input data samples may thus vary accordingly.

FIG. 1 depicts a method for building a machine-learned classifier. The method 100 is computer-implemented. The method 100 may be implemented by any type of computer. The method 100 includes a number of acts implemented by a processor, e.g., a processor of the computer. The configuration of the processor may thus vary. The processor may or may not be involved in use of the machine-learned classifier, e.g., application of the machine-learned classifier to incoming data to be classified. The computer and/or processor thus may or may not be associated with (e.g., a component of) an imaging system or other apparatus directed to acquiring training data or other input data.

The method 100 may begin with an act 102 directed to obtaining a plurality of training data samples. Each training input sample is associated with one of a plurality of classes. For instance, each training data sample may have been classified by a radiologist or other expert, and/or via any other classification technique. In air trapping examples, each training input sample may be classified in one of two classes, e.g., a first class that exhibits air trapping and a second class that does not exhibit air trapping. In donor lung screening examples, each input sample may be classified as either suitable for transplant or not suitable for transplant.

Each data sample may be representative of, and/or otherwise include, scan or other image data. For instance, each input data sample may be representative of tissue in one of multiple views. Each view may be a cross-sectional view. For instance, each view may correspond with a respective cross-section of the tissue. Cross-sectional views may include, for example, the sagittal, coronal, and axial sections. The multiple views may include fewer, additional, or alternative views, including other types of views and/or data. The number and dimensionality of the views may vary accordingly. For instance, the data samples may include data in addition or alternative to image data. Examples of non-image data include physiological data and various types of multi-dimensional data in non-medical applications. The nature of the data may thus vary in other ways in accordance with the context or nature of the classification.

In some cases, the act 102 includes acquiring three-dimensional image data in an act 103. The three-dimensional image data may be acquired by a CT scanner. The CT scanner may be integrated with the computer or processor implementing the method 100 to any desired extent. Alternative or additional scanners or imaging systems may be used, including, for instance, a magnetic resonance imaging (MRI) system. Additional or alternative data acquisition units may be used in cases in which the training data includes non-image data. In still other cases, the training data has been previously acquired. In such cases, the act 102 may include accessing one or more data storage devices or other memories on which the training data is stored.

The method 100 may include pre-processing the training data in an act 104. The act 104 may include the implementation of one or more data processing procedures. In the example of FIG. 1, the procedures include image segmentation of 2D slices (or other scan data) in an act 106, image smoothing in an act 108, image de-noising in an act 110, image thresholding in an act 112, and one or more other filtering procedures in an act 114. The de-noising may be useful to reduce textures within the tissue (e.g., lung tissue) and other noise in the images. The thresholding may involve or otherwise include histogram thresholding. Other filters include morphological filters configured to support better segmentation. The order in which the procedures are implemented may vary. For instance, image segmentation may follow one or more of the other acts. Additional, fewer, or alternative procedures may be implemented. For instance, the pre-processing may vary in accordance with the nature of the training data.

The training data may be sampled in an act 116 to generate a plurality of data samples of the training data. In some cases, the sampling may involve or otherwise include defining a number of voxels in an act 118. Respective portions of three-dimensional image data, including, for instance, respective areas of underlying two-dimensional slices, may thus be assigned or apportioned across the voxels. For each voxel, patch data (e.g., two-dimensional patch data) may then be defined or otherwise generated in an act 120 for each view (e.g., cross-sectional view). Each training input data sample may thus be or include a training data patch. Each training data patch, in turn, includes image data representative of a two-dimensional slice in one of the multiple cross-sectional views. For example, each training data patch may be or include an image region having a size of 15 pixels by 15 pixels. The number of pixels may vary in other examples. Alternatively or additionally, one or more aspects of the sampling may have been previously implemented, in which case the training data obtained for the method 100 (e.g., in the act 102) may be or otherwise include sampled training data.

In an act 122, a sparse code-based optimization is implemented to build a set of composite dictionaries of the machine-learned classifier based on the plurality of data samples of the training data. Each composite dictionary is representative of one of the plurality of classes. As described herein, each composite dictionary includes a plurality of constituent dictionaries. Each constituent dictionary, in turn, is associated with a respective one of the multiple views. Each composite dictionary may accordingly be considered to be a multi-view dictionary. As described herein, the integration of the constituent dictionaries into a composite dictionary allows the composite dictionary to be applied during use to any image patch regardless of the view (e.g., cross-sectional view) of the image patch.

Each dictionary may be configured as, or otherwise include, a matrix. In one example, the matrix may include 25 rows and 256 columns. Each element of the matrix may be a real number, as described below. In some cases, the constituent dictionaries are arranged in respective columns of the matrix. For example, the constituent dictionary for the first view is set forth in the first 64 columns. The constituent dictionary for the second view is then set forth in the next 64 columns, and so on. The vector in each column may be considered a respective one of the bases of the dictionary.

The act 122 may include an act 124 in which bases of each composite dictionary are iteratively updated in accordance with a minimization problem. As described below, the minimization problem may include two components. A first component is directed to minimizing differences of the training data samples associated with the class for which the respective composite dictionary is representative. A second component is directed to maximizing differences between the training data samples associated with a different class for which the respective composite dictionary is not representative. The components are combined in the minimization problem. For instance, the second component may be subtracted from the first component. In some cases, the second component is scaled by a regularization parameter.

The optimization may be configured to include the implementation of a number of procedures. In the example of FIG. 1, iteratively updating the bases includes an act 126 in which a block coordinate descent procedure is implemented to update the bases one at a time. Alternatively or additionally, the act 122 includes iteratively updating sparse codes for the plurality of training data samples. The sparse code for each training data sample may be configured as, or otherwise include, a vector. Each element of the vector may be a code (e.g., a binary code, either 1 or 0). The vector is often mostly composed of zeros, hence the sparsity of the code. Further details regarding the sparse codes are set forth below.

Iteratively updating the sparse codes may include implementing an orthogonal matching pursuit (OMP) procedure in an act 128. In some cases, the sparse-code base optimization involves or otherwise includes an act 130 in which the optimization alternates between iteratively updating dictionary bases of a respective one of the set of composite dictionaries for a given set of the sparse codes and iteratively updating the sparse codes for a given set of the dictionary bases. Further details regarding these procedures are provided in connection with a number of examples below.

The method 100 may include one or more additional, fewer, or alternative acts. For example, one or more of the pre-processing acts may not be implemented in the event that the training data obtained has already been filtered. In another example, the training data obtained in the act 102 may already be sampled.

Figure 2:
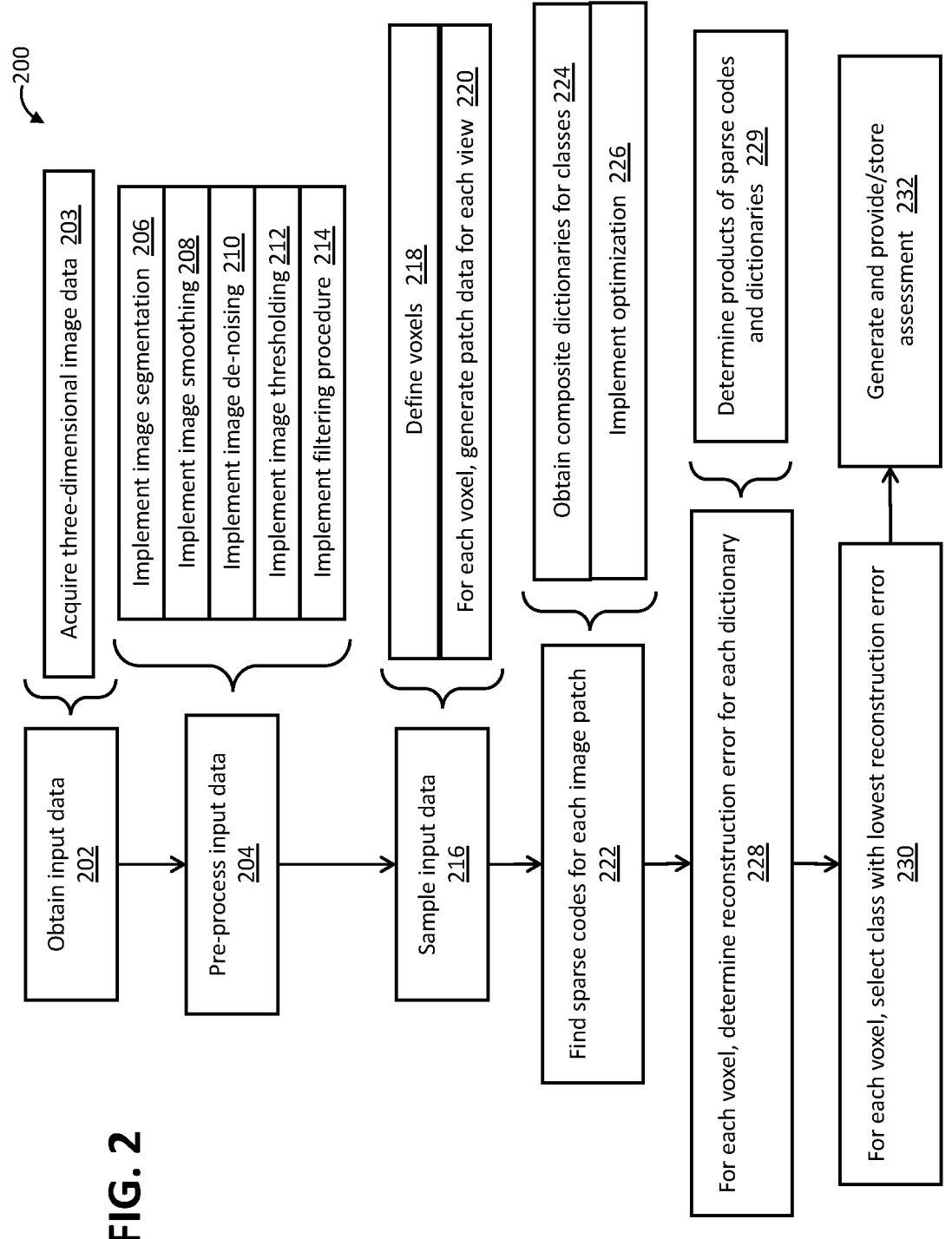
FIG. 2 is a flow diagram of a computer-implemented method of tissue assessment based on a plurality of machine-learned composite dictionaries in accordance with one example.

FIG. 2 depicts a method 200 of tissue assessment or abnormality detection. The method 200 is computer-implemented. The method 200 may be implemented by any type of computer. The method 200 includes a number of acts implemented by a processor, e.g., a processor of the computer. The configuration of the processor may thus vary. The method 200 may be implemented by the same processor used to implement the training method (e.g., the method 100 of FIG. 1), and/or another processor. The method 200 may be configured to provide other types of assessments in cases involving other types of input data (e.g., non-image data or data not indicative of tissue).

The method 200 may begin with an act 202 in which input data is obtained for abnormality detection or other assessment. In some cases, the act 202 includes an act 203 in which three-dimensional image data of the tissue is acquired with a scanner, such as a CT scanner. Alternatively or additionally, the image data is obtained via accessing a data storage or other memory. In such cases, a number of input data samples may be obtained, insofar as the input data may have been already sampled and otherwise processed in preparation for the assessment.

Each input data sample may be representative of tissue in one of multiple views (e.g., cross-sectional views), as described above. For instance, as described herein, the multiple views may include respective cross-sectional views of three-dimensional image data. Alternative or additional types of input data may be used, including, for instance, non-image data.

The method 100 may include pre-processing the training data in an act 204. The pre-processing may or may not be similar to the procedures described above in connection with the training data. In the example of FIG. 2, the procedures include image segmentation of 2D slices (or other scan data) in an act 206, image smoothing in an act 208, image de-noising in an act 210, image thresholding in an act 212, and one or more other filtering procedures in an act 214. As described above, the order in which the procedures are implemented may vary. For instance, image segmentation may follow one or more of the other acts. Additional, fewer, or alternative procedures may be implemented. For instance, the pre-processing may vary in accordance with the nature of the training data.

The input data may be sampled in an act 216 to generate a plurality of data samples of the input data. In some cases, the sampling may involve or otherwise include defining a number of voxels in an act 218. Respective portions of three-dimensional image data, including, for instance, respective areas of underlying two-dimensional slices, may thus be assigned or apportioned across the voxels. For each voxel, patch data (e.g., two-dimensional patch data) may then be defined or otherwise generated in an act 220 for each view (e.g., cross-sectional view). Each input data sample may thus be or include an input data patch. The input data patches may or may not be overlapping. Each input data patch includes image data representative of a two-dimensional slice in one of the multiple cross-sectional views. For example, each input data patch may be or include an image region having a size of 15 pixels by 15 pixels. The number of pixels may vary in other examples. Alternatively or additionally, one or more aspects of the sampling may have been previously implemented, in which case the input data obtained for the method 200 (e.g., in the act 202) may be or otherwise include sampled input data.

The method 200 includes a number of acts directed to processing the input data. Such processing of the input data patches or other samples may be implemented in a serial or parallel manner. For instance, in some cases, the processing may be implemented for a specific patch. The result may thus be or include a classification or assessment for the specific patch. Each image patch may then be processed serially. Upon the completion of such serial processing, an overall classification or assessment for the input data may be generated based on the individual assessments. In other cases, the processing of specific patches is implemented concurrently or otherwise in parallel, in which case individual assessments for specific patches may or may not be generated.

In an act 222, a set of sparse codes is found or otherwise determined for each input data sample. The set of sparse codes is determined based on the set of machine-learned composite dictionaries, e.g., the dictionaries built via the method 100 of FIG. 1. To that end, the composite dictionaries for the classes may be accessed from a memory or otherwise obtained in an act 224. An optimization based on each machine-learned composite dictionary may then be implemented in an act 226. As described herein, each machine-learned composite dictionary includes a plurality of constituent dictionaries, with each constituent dictionary being associated with a respective one of the multiple views. However, because the optimization is a joint optimization, the set of sparse codes are collectively representative of all of the multiple cross-sectional views. As described herein, the optimization includes a joint $I_{12}$ norm minimization calculation. The minimization may be used to calculate the set of sparse codes. Further details regarding the optimization are provided below in connection with a number of examples.

A number of examples are described below in connection with the detection of abnormalities in lung tissue. In such cases, one dictionary of the set of machine-learned composite dictionaries may be representative of images of abnormal lung tissue. Another dictionary is then representative of images of healthy, or not abnormal, lung tissue. In some cases, the dictionaries may be configured such that the images of abnormal lung tissue are indicative of a presence of air-trapping, while the images of healthy lung tissue are indicative of an absence of air-trapping. The nature of the images may vary in other cases. The number of dictionaries may also vary in accordance with whether different types of abnormalities are being detected.

Once the set of sparse codes is determined for the input data, a reconstruction error is calculated in an act 228 for the set of sparse codes relative to each machine-learned composite dictionary. The act 228 may include an act 229 in which a product is determined for each sparse code and composite dictionary. For instance, the product may be or otherwise include a multiplication product. Further details are provided below in connection with a number of examples.

The classification of the input data may then be determined in an act 230 based on which composite dictionary has the lowest, or minimum, reconstruction error for the set of sparse codes. The input data is assigned to the class having the lowest reconstruction error. Further details regarding the reconstruction error calculation are provided below in connection with a number of examples.

In an act 232, a tissue assessment is generated in accordance with the assigned or selected machine-learned composite dictionary with the minimum reconstruction error. In some cases, the tissue assessment is for a particular voxel or other tissue sample portion. In other cases, the tissue assessment involves the compilation of the voxel-specific classifications. In such cases, the tissue assessment may be determined by compiling the number of voxels assigned to each class, and using a threshold or other calculation to determine the overall assessment. For example, a lung may be classified as unsuitable for transplant if the compilation reveals that more than 30% of the voxels are classified as unhealthy. Other thresholds and compilation techniques may be used.

The tissue assessment may involve or otherwise include a prediction of therapeutic outcome. For example, in lung transplant cases, the prediction of therapeutic outcome may be related to or otherwise be indicative of length of stay in an intensive care unit (e.g., after the transplant operation). As explained below in connection with one or more examples that were applied to data from past lung transplant operations, lungs that were classified as unsuitable (i.e., a positive classification), but were, in fact, used (i.e., implanted, a false positive classification), resulted in longer intensive care unit stays. In these and other cases, the tissue assessment may thus be used to predict a therapeutic outcome. A wide variety of therapeutic procedures may thus be addressed via the tissue assessment. Such tissue assessments may have classifications directed to, for instance, "most responsive to therapy/procedure" and "less responsive to therapy/procedure."

The act 232 may also include providing the tissue assessment via an output device, such as a monitor of the computer or other processor implementing the method 200. Alternatively or additionally, the tissue assessment may be provided by storing data on a storage device or other memory.

Further details regarding the machine-learning based classification provided by the disclosed methods are now set forth in connection with a number of examples. The examples depict the manner in which the disclosed methods provide a multi-view task-driven dictionary learning procedure. The procedure is configured to learn discriminative dictionaries for each class from multiple views of the data in a joint fashion by imposing group sparsity constraints. The examples exhibit the manner in which the disclosed methods provide (1) an efficient multi-view discriminative dictionary learning procedure that emphasizes inter-class differences while keeping intra-class differences small, resulting in enhanced classification performance, and (2) a framework that facilitates more flexible fusion of information from multiple views at the feature level by allowing the images from different views to have different sparsity patterns when learning the dictionary. The examples involve AT image classification on expiratory CT images.

The following notations are used herein in describing the training and use of the machine-learning based classifier. Let c be the total number of classes. In the AT classification case, the classification is a binary classification problem. For example, c can be 2, where class 1 refers to the AT areas and class 2 refers to the background. Let v be the total number of views in which the data is scanned or otherwise visualized. In this example, the views are the axial, coronal, or sagittal cross-sectional views of three-dimensional images. Let $x^m$ denote a vectorized image patch in the view m. For i=1, . . . , c, and m=1, . . . , v, let $$X_i^m \in \mathbb{R}^{d \times N_i^m}$$

and $$\tilde{X}_i^m \in \mathbb{R}^{d \times \tilde{N}_i^m}$$

be matrices containing all the vectorized patches from class i in the view m and its complementary classes, respectively. Each constituent dictionary of class i in the view m is denoted $$D_i^m \in \mathbb{R}^{d \times k_i^m}.$$

The $I_q$ norm of a sparse code $\alpha$ may be denoted as follows:

$$\|\alpha\|_{l_q} = \left\{ \sum_{j=1}^{k} |\alpha_j|^q \right\}^{1/q}.$$

Then the $I_{1q}$ norm of a sparse matrix A is defined as follows:

$$\|A\|_{l_{1q}} = \sum_{j=1}^{k} \|\alpha_j\|_{l_q}.$$

The sparse matrix $\Lambda$ may thus be considered a compilation of the sparse codes across all of the training image patches. The training image patches may be obtained from multiple images and collected together.

An example of the multi-view task-driven dictionary learning procedure is now described. The procedure is configured to build class-specific, composite dictionaries $D_i$ such that each composite dictionary $D_i$ represents the patches from class i reasonably well, but also at the same time represents the patches from the other classes quite poorly. For example, for the learnt dictionaries, this characteristic may be expressed as wanting:

$$\sum_{m=1}^{v} \left\{ \frac{1}{N_i^m} \min_{\{\|\Lambda_i^m\|_0 \leq L_i^m\}} \|X_i^m - D_i^m \Lambda_i^m\|_F^2 \right\} \text{ to be small and}$$

$$\sum_{m=1}^{v} \left\{ \frac{1}{\tilde{N}_i^m} \min_{\{\|\tilde{\Lambda}_i^m\|_0 \leq L_i^m\}} \|\tilde{X}_i^m - D_i^m \tilde{\Lambda}_i^m\|_F^2 \right\} \text{ to be large}$$

where $$L_i^m$$

controls the sparsity level of each view m and $\|\cdot\|_F$ denotes the Frobenius norm. For simplicity in notation, only one class is considered. So the index i in the notation may be dropped, such that the following notations may be used:

$Y^m$, $D^m$, $\Lambda^m$, $\tilde{\Lambda}^m$, $N^m$, $\tilde{N}^m$, and $L^m$.

Then the optimization problem for each dictionary may be formulated as:

$$D^* = \operatorname*{argmin}_{D} \left[ \sum_{m=1}^{v} \left\{ \frac{1}{N^m} \min_{\|\Lambda^m\| \leq L^m} \|X^m - D^m \Lambda^m\|_F^2 \right\} - \right. \tag{1}$$

$$\left. \sum_{m=1}^{v} \left\{ \frac{\gamma}{\tilde{N}^m} \min_{\|\tilde{\Lambda}^m\| \leq L^m} \|\tilde{X}^m - D^m \tilde{\Lambda}^m\|_F^2 \right\} \right]$$

where the composite dictionary $D=[D^1, \ldots, D^v]$, and $\gamma$ is a positive regularization parameter. The first term in equation (1) minimizes the intra-class differences and the second term in equation (1) emphasizes the inter-class differences. By solving the above problem in equation (1), the appropriate dictionaries may be found.

Figure 3:
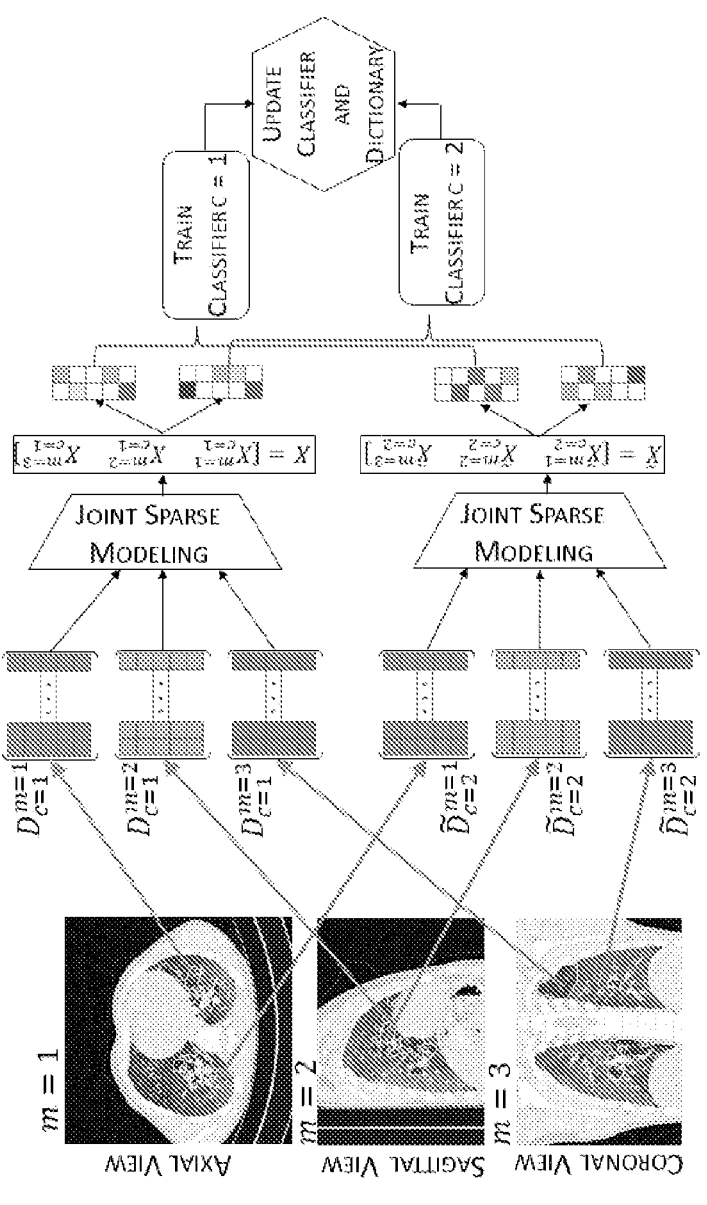
FIG. 3 is a schematic view of a computer-implemented method for building a machine-learned classifier using sparse code-based optimization in accordance with one example.

FIG. 3 depicts an example of the dictionary learning and classifier training procedure. In this example, composite dictionaries are provided for classes 1 and 2. Each composite dictionary includes constituent dictionaries for views 1, 2, and 3, which correspond to the axial, sagittal, and coronal cross-sectional views. During learning, the constituent dictionaries are provided to a joint sparse modeling procedure, an example of which is described below.

Once the dictionaries are learned, a new image patch x from a test image may be classified via sparse representation-based classification. First, the sparse codes $\hat{\alpha}$ for an incoming image patch are calculated via a joint $I_{12}$ norm minimization as follows:

$$\hat{\alpha} = \operatorname*{argmin}_{\alpha} \left[ \sum_{m=1}^{v} \{\|x^m - D_T \alpha^m\|_2^2\} + \rho_1 \|\Lambda\|_{l_{12}} + \rho_2 \|\Lambda\|_{l_{11}} \right] \tag{2}$$

where the matrix $$D_T = [D_1^1, \ldots, D_c^1, \ldots, D_1^v, \ldots, D_c^v]$$

is the compilation of all of the composite dictionaries, and where $\alpha = [\alpha^1, \ldots, \alpha^v]$, and where $\rho_1$ and $\rho_2$ are scalar constants. The scalar constants serve as regularization parameters. Next, the right class of image patch x is identified in the following manner:

$$\hat{c} = \underset{1 \leq i \leq c}{\operatorname{argmin}} \{\delta_i(x)\}$$

where $\delta_i(x) = \|x - D_i \delta_i(\hat{\alpha})\|$, and where $\delta_i(\hat{\alpha})$ is part of $\hat{\alpha}$ associated with the class i.

Further details regarding an example of a dictionary training procedure are now provided. In this example, an iterative procedure is used to find an optimal solution for equation (1). Because the problem is non-convex in both D and $\Lambda$ together, the process is iterated first by fixing D while optimizing $\Lambda$, $\tilde{\Lambda}$, and vice-versa.

In a sparse coding step, the matrices $\Lambda^*$, $\tilde{\Lambda}^*$ are found by solving the following:

$$\Lambda^* = \underset{\|\Lambda\|_0 \leq L}{\operatorname{argmin}} \sum_{m=1}^{v} \{\|X^m - D^m \Lambda^m\|_F^2\};$$

$$\tilde{\Lambda}^* = \underset{\|\tilde{\Lambda}\|_0 \leq L}{\operatorname{argmin}} \sum_{m=1}^{v} \{\|\tilde{X}^m - D^m \tilde{\Lambda}^m\|_F^2\}$$

With the same dictionary D, these two sparse coding optimization problems may be combined into a single optimization problem as follows:

$$\hat{\Lambda}^* = \underset{\|\hat{\Lambda}\|_0 \leq L}{\operatorname{argmin}} \sum_{m=1}^{v} \{\hat{X}^m - D^m \hat{\Lambda}^m\|_F^2\} \tag{4}$$

where $\hat{X}^m = [X^m, \tilde{X}^m]$ is the matrix with all of the training image patches and $\hat{\Lambda}^m = [\Lambda^m, \tilde{\Lambda}^m]$. This sparse coding optimization problem may be solved using the orthogonal matching pursuit (OMP) technique. For example, a sparse modeling software toolbox such as SPAMS may be used to implement the technique.

Further details regarding updating bases of the dictionaries are now provided in connection with one or more examples. For updating the dictionary bases, a matrix D* is determined by solving the following optimization problem:

$$D^* = \underset{D}{\operatorname{argmin}} \left[ \sum_{m=1}^{v} \left\{ \frac{1}{N^m} \|X^m - D^m \Lambda^m\|_F^2 \right\} - \sum_{m=1}^{v} \left\{ \frac{\gamma}{N^m} \|\tilde{X}^m - D^m \tilde{\Lambda}^m\|_F^2 \right\} \right] \tag{5}$$

In some cases, the block coordinate descent technique may be used to solve the optimization problem to update the bases one at a time. A warm start may be used. Using the fact that $$\|Y\|_F^2 = \operatorname{trace}(YY^\top)$$

for any matrix Y, the expression (5) may be simplified to the following:

$$D^* = \underset{D}{\operatorname{argmin}} \left[ \sum_{m=1}^{v} \{-2\operatorname{trace}(G^m D^{m\top}) + \operatorname{trace}(D^m H^m D^{m\top})\} \right] \tag{6}$$

where $$G = \frac{1}{N} X \Lambda^\top - \frac{\gamma}{\tilde{N}} \tilde{X} \tilde{\Lambda}^\top \text{ and } H = \frac{1}{N} \Lambda \Lambda^\top - \frac{\gamma}{\tilde{N}} \tilde{\Lambda} \tilde{\Lambda}^\top$$

in each view v.

A positive semi-definite (PSD) constraint may be imposed upon the symmetric matrix H. The constraint ensures that the optimization problem in expression (6) is tractable and may be solved efficiently. The constraint also establishes that $-2$ trace $(GD^T) + \operatorname{trace}(DHD^T)$ is a convex function with respect to D. The PSD constraint of the symmetric matrix H is equivalent to the non-negativity constraint of $\lambda_1(H)$, where $\lambda_1(H) \leq \lambda_2(H) \leq \ldots \leq \lambda_{max}(H)$ are the eigenvalues of the matrix H. The lower bound for $\lambda_1(H)$ is given by the following expression $$\lambda_0 = \frac{1}{N} \lambda_1(\Lambda \Lambda^\top) - \frac{\gamma}{\tilde{N}} \lambda_{max}(\tilde{\Lambda}\tilde{\Lambda}^\top) \leq \lambda_1(H)$$

using Weyl's inequalities. Consequently, if the regularization parameter $\gamma$ is small enough such that $\lambda_0 \geq 0$, then H is PSD.

In order to ensure that H is PSD, the dictionary learning procedure is configured to ensure that the value of the regularization parameter $\gamma$ is sufficiently small. In one example, the dictionary learning procedure may be implemented as follows.

```
input: X^m, X̃^m, ρ₁, ρ₂, γ, L, k
output: D*
1     Initialize D^m by randomly selecting k columns of X^m
          for all m ∈ {1, . . . , v}
2   while not converged do
3     |  Fix D = D* and update Λ, Λ̃ by solving (4);
4     |  Fix Λ, Λ̃, and calculate:
      |     G = 1/N XΛ^T − γ/Ñ X̃Λ̃^T; H = 1/N ΛΛ^T − γ/Ñ Λ̃Λ̃^T;
5     |  if H is not PSD then
6     |  |  γ ← 0.9 γ ;
7     |  |  go to 4;
8     |  else
9     |  |_  Update D by solving (6);
      |_
```

Figure 4:
FIG. 4 depicts example images of lung tissue for air trapping classification using the computer-implemented tissue assessment method of FIG. 2, the images being in different dimensions and having dark areas within the lung region to be classified.

FIG. 4 depicts sample images from a dataset to which an example of the dictionary learning classifier of the disclosed methods has been applied for classification and assessment in connection with air trapping (AT) in lungs. Areas with AT are class 1. Areas without AT are class 2. The dataset includes three-dimensional expiratory CT images (N=32) from eight cystic fibrosis (CF) school-age children at baseline, 3, 12, and 24 months. The size of each two-dimensional slice in the three-dimensional dataset is 512×512 pixels. There were about 700-750 slices in each three-dimensional dataset. A manual segmentation and classification of all the AT areas within these images was performed by an expert and considered as ground truth for subsequent analysis.

In this example, each of the three-dimensional images within the dataset includes several locations of AT areas present within them. Two (N=8) out of the total eight images (25% of the data) for training and the remaining six (N=24) images (75% of the data) for testing at random. During training, a number (e.g., 1,000,000) of non-overlapping image patches, each having a pixel size of 11×11, were selected from areas within the lung having AT (class 1) and not having AT (class 2).

Figure 5:
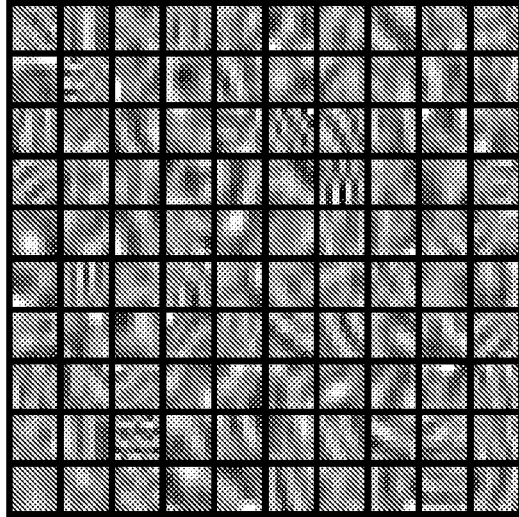
FIG. 5 depicts images of example bases of two learnt dictionaries for a class associated with air trapping areas and for a class associated with the absence of air trapping areas.
Figure 5:
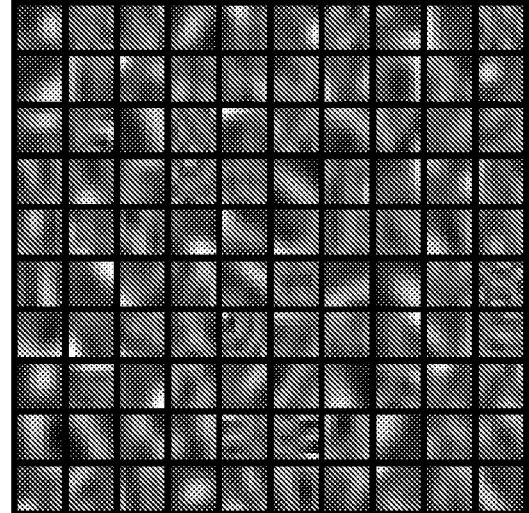

In the sparse coding stage, the regularization parameters are set as follows: $\rho_1$=0:01; and $\rho_2$=0:05. For dictionary learning, the regularization parameter $\gamma$ is set to 0:001 initially. The number of dictionary bases in each dictionary to be learnt is set to k=256. A sparsity level of L=12 is also selected. In order to reduce the effect of over-training and make the classifier generalize well, the training is repeated five times with an arbitrary choice of selecting the training and testing images each time. The results are reported below as an average of the classification accuracies over 5 repetitions. The learnt dictionary bases corresponding to the two classes (AT and no AT) within the lungs in the CT images are visualized in FIG. 5.

The performance of the classifier configured with the learnt dictionaries was compared with other types of classifiers, including a SVM classifier, a MLP classifier, and a PCA-based deep learning classifier (e.g., PCANet). The SVM, MLP, and PCANet classifiers, as well as the dictionary learning classifier of the disclosed methods, were tested on 75% of the dataset. The classifiers were evaluated sing the following metrics: precision P; recall R; receiver operating characteristic (ROC) curves, area under the curve (AUC), and coverage measure (FB-score).

The precision P and recall R metrics are determined as follows:

$$P = \frac{TP}{TP + FP}, R = \frac{TP}{TP + FN} \quad (7)$$

where TP is the number of true positive classifications, FP is the number of false positive classifications, and FN is the number of false negative classifications.

An ROC curve is a plot between the true positive rate (e.g., sensitivity or recall (R)), which is defined by expression (7), and the false positive rate (e.g., the complement of specificity), which is defined as FP/(FP+FN).

The coverage measure, also commonly known as the FB-score is defined as follows:

$$F_\beta = \left(1 + \beta^2\right)\frac{PR}{\left(\beta^2 P\right) + R} \quad (8)$$

The measure $F_1$ (i.e., F$\beta$=1) may be used for this type of evaluation.

The AUC is the average of precision P(R) over the interval (0≤R≤1), where P(R) is a function of recall R. It is determined by the following expression:

$$AUC = \int_0^1 P(R)dR. \quad (9)$$

The best classifier among the several alternatives may be the one that maximizes either the AUC or the F$\beta$-score.

Table I shows the average precision (P), recall (R), AUC, and F$\beta$-score values for all the classifiers on the test data. As shown in Table I, the F$\beta$-score of the classifier of the disclosed methods is 8.96 percentage points greater than the SVM classifier, 7.09 percentage points greater than the MLP classifier, and 4.07 percentage points greater than the PCANet classifier. Table I also shows that the classifier of the disclosed methods has the largest AUC among all the evaluated methods.

TABLE I

| PERFORMANCE OF THE CLASSIFICATION ALGORITHMS | | | | |
| --- | --- | --- | --- | --- |
| Methods | Precision (P) | Recall (R) | AUC | F$\beta$-score |
| Our Method | 0.9143 | 0.8762 | 0.8654 | 0.8948 |
| SVM | 0.8148 | 0.7959 | 0.7891 | 0.8052 |
| MLP | 0.8436 | 0.8052 | 0.8103 | 0.8239 |
| PCANet | 0.8619 | 0.8465 | 0.8211 | 0.8541 |

Figure 6:
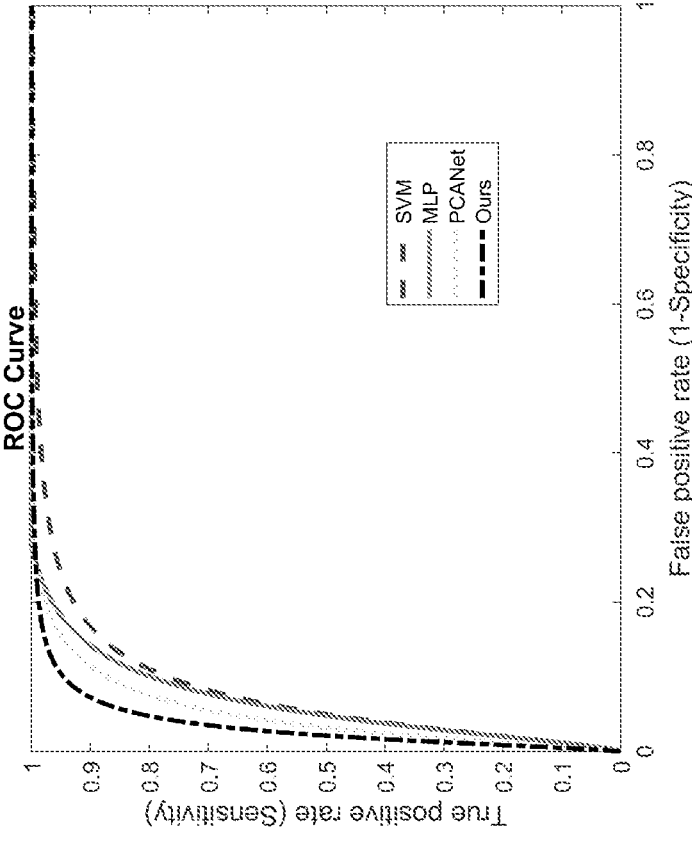
FIG. 6 is a graphical plot of receiver operating characteristic (ROC) curves comparing a number of different classification methods, including a classification method involving a plurality of machine-learned composite dictionaries in accordance with one example.

FIG. 6 shows the ROC curves for all the methods under comparison. As shown, the classifier of the disclosed methods has better classification accuracy relative to the other classifiers at all points along the curve.

The classifier of the disclosed methods thus provides accurate classification of AT within expiratory thoracic CT images. As described herein, the classifier is or includes a multi-view task-driven dictionary learning classifier. With this classifier, the disclosed methods are capable of classifying the AT areas of interest within the expiratory CT images, distinguishing such areas from the other normal areas of the lung. The classifier may be used for classifying other types of image patches. As described above, the classifier benefits from a discriminative dictionary learning procedure that learns features that are very different for each class, by emphasizing intra-class variations while keeping the differences between class large.

Figure 7:
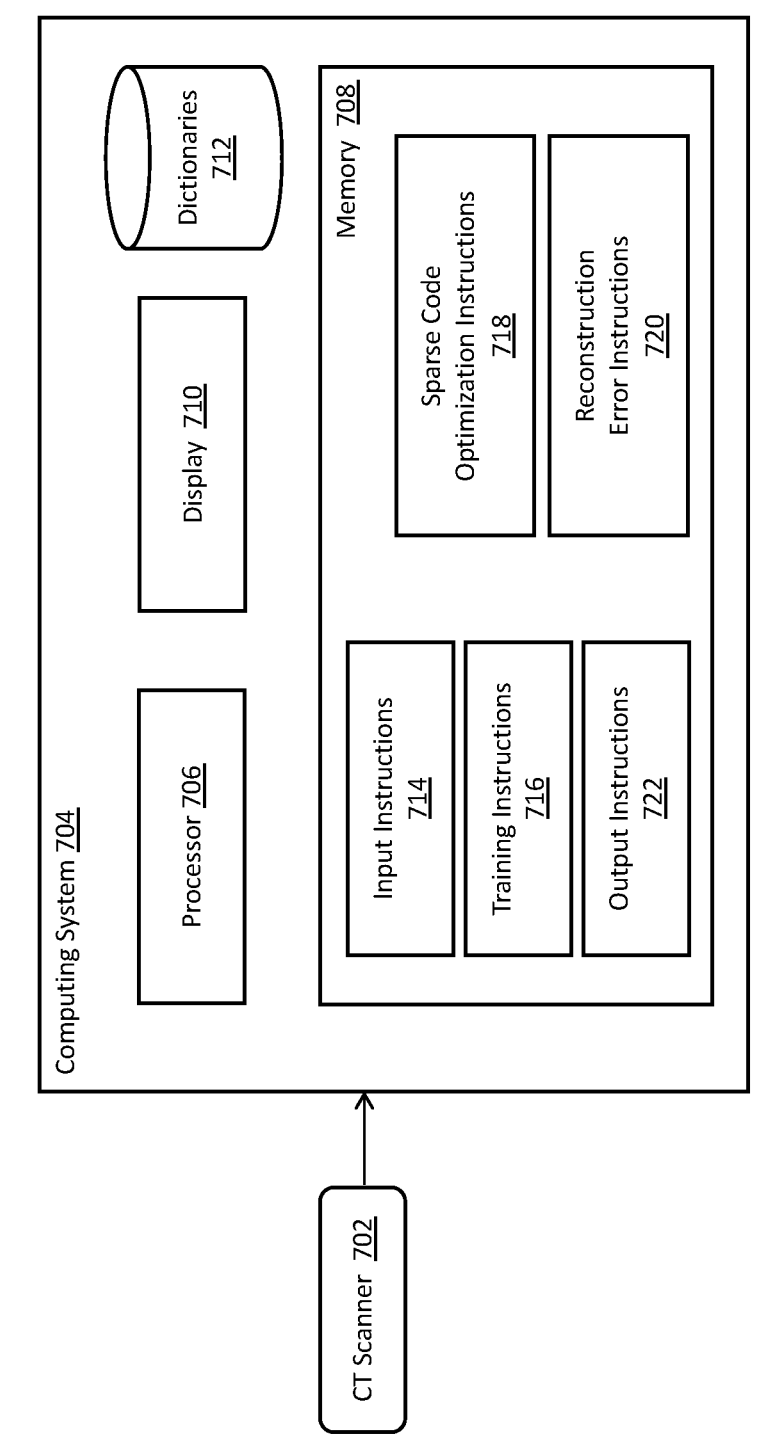
FIG. 7 is a schematic diagram of a system of tissue assessment involving the application of a plurality of machine-learned composite dictionaries to images captured by a CT scanner in accordance with one example.

FIG. 7 depicts a system 700 for tissue assessment. The system 700 may be used to implement one of the tissue assessment methods described herein and/or another method. The system 700 may alternatively or additionally be used to implement one of the classifier building methods described herein.

The system 700 includes a scanner 702 configured to capture scan data representative of tissue in multiple views. In the example of FIG. 7, the scanner 702 is or includes a CT scanner. Other image acquisition systems may be used, including, for instance, an MRI system, to acquire or otherwise capture the scan data. Alternative or additional devices or systems may be used to acquire input data (e.g., non-scan input data) for the system 700. The nature of the input data may vary accordingly.

In the example of FIG. 7, the system 700 includes a computing system 704. The computing system 704 may or may not be integrated with the CT scanner and/or other input data acquisition system or device. The extent of integration may vary to any desired extent. The computing system 704 includes one or more processors 706, one or more memories 708 coupled to the processor 706, a display 710, and one or more storage units 712. The memory 706 is used to store instructions or instruction sets to be executed on the processor 706. In this example, input instructions 714, training instructions 716, sparse code optimization instructions 718, reconstruction error instructions 720, and output instructions 722 are stored on the memory 708. The instructions or instruction sets may be integrated with one another to any desired extent. A set of machine-learned composite dictionaries is stored on the storage device 712. As described herein, each machine-learned composite dictionary of the set of machine-learned composite dictionaries includes a plurality of constituent dictionaries. Each constituent dictionary of the plurality of constituent dictionaries is associated with a respective one of the multiple views.

The execution of the instructions by the processor 706 may cause the processor to implement one or more of the methods described herein. In this example, the processor 706 is configured to execute the input instructions 714 to generate a plurality of input data samples based on the scan data. The processor 706 is configured to execute the sparse code optimization instructions 718 to determine a set of sparse codes for each input data sample of the plurality of input data samples. The set of sparse codes may be determined based on the composite dictionaries in the storage device 712. The composite dictionaries may be generated as described herein via execution of the training instructions 716. The processor 706 is configured to execute the reconstruction error instructions 720 to determine a reconstruction error for the set of sparse codes relative to each machine-learned composite dictionary of the set of machine-learned composite dictionaries. The processor 706 is configured to execute the output instructions 722 to provide the tissue assessment in accordance with the machine-learned composite dictionary in the set of machine-learned composite dictionaries having a minimum reconstruction error of the determined reconstruction errors. In this example, the tissue assessment may be provided via the display 710 and/or stored in the memory 708, the storage device 712.

The system 700 may include fewer, additional, or alternative elements. For instance, the system 700 may include one or more components directed to network or other communications between the CT scanner 702, the computing system 704, and/or other input data acquisition or computing components.

Figure 8:
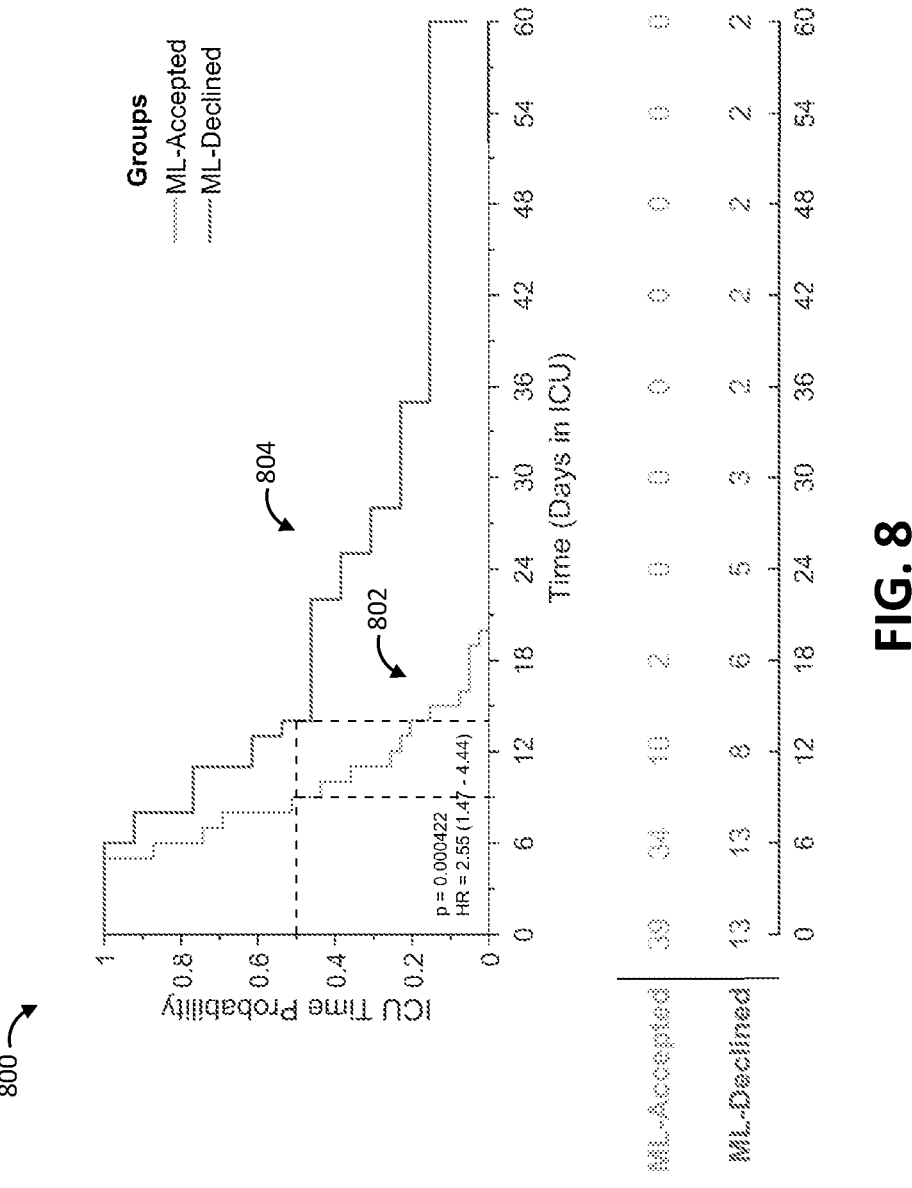
FIG. 8 depicts a graphical plot of intensive care unit (ICU) time probability for accepted lungs (i.e., lungs that were used in transplant procedures) for different classifications by the disclosed methods and systems, along with a table of the underlying ICU length of stay data.

FIG. 8 and Table II below provide an example of the application of the disclosed methods and systems to a tissue assessment involving a prediction of therapeutic outcome. In this example, the prediction of therapeutic outcome is indicative of length of stay in an intensive care unit (e.g., after the transplant operation).

In this example, the disclosed methods and systems was trained on the final decision for transplantation. Upon implementation, a number of false positives were observed. As shown in Table II below, of the 52 donor lungs found to be acceptable for transplantation, around 20% were predicted to be unacceptable (i.e., declined by the model; hereafter "ML Declined"). As shown in Table II, ML Declined donor lungs had feature probabilities significantly lower (0.205+/− 0.042) than those accepted by the model ("ML Accepted") for transplant (0.637+/−0.134, p<0.0001). Stratifying the donors based on the predictions, no significant differences in donor characteristics were found, as shown in Table II.

Nevertheless, and unexpectedly, post-transplant outcomes of recipients were found to differ between predicted groups of transplanted lungs. Hospital and ICU stay post-transplant were both found to be significant (p=0.039 and 0.0004, respectively).

FIG. 8 depicts a Kaplan Meier plot 800 that demonstrates that those recipients that received an ML Declined donor lung had a median ICU stay of 5 days (95% confidence interval) longer than those who received ML Accepted lungs. The ICU time probabilities for ML Accepted lungs and ML Declined lungs are depicted along plot lines 802, 804, respectively.

Table II—Donor Characteristics and Post-Transplant metrics from accepted lungs

| Transplanted Cohort | False Positive | True Positive | P value |
|---|---|---|---|
| Donor, N | 13 | 39 | |
| Feature Probability | 0.205 (0.042) | 0.637 (0.134) | <0.0001 |
| Age (years) | 55 (14) | 49 (16) | 0.166 |
| Male, N (%) | 8 (62) | 24 (62) | 1.000 |
| Donor weight (kg) | 76 (10) | 172 (11) | 0.923 |
| Donor height (cm) | 78 (18) | 173 (7) | 0.639 |
| Packyears | 1 (0) | 1 (0) | 0.910 |
| Post-Transplantation | | | |
| Highest PGD Score, N | | | 0.06 |
| 0 | 0 | 3 | |
| 1 | 2 | 7 | |
| 2 | 0 | 9 | |
| 3 | 11 | 20 | |
| Hospital Stay (days) | 43 (24) | 29 (9) | 0.039 |
| Days till Extubation (days) | 4 (5) | 2 (1) | 0.239 |
| ICU Stay (days) | 23 (19) | 10 (4) | 0.004 |

As shown via the example of FIG. 8, the tissue assessment provided via the disclosed methods and systems may be used to predict a therapeutic outcome. The disclosed methods and systems are not limited to lung transplant-related outcomes. Other therapeutic procedures may thus be addressed via classifications such as "higher likelihood of success via therapy/procedure" and "lower likelihood of success via therapy/procedure."

Described above are methods and systems for various classifications, including, for instance, classification of air-trapping (AT) within expiratory thoracic computed tomography (CT) images. The disclosed methods and systems may be used to assess other tissue conditions, including, e.g., other progressive lung diseases. The classifications generated by the disclosed methods and systems are based on an automated feature extraction framework via multi-view task-driven dictionary learning. The extraction framework presents a low complexity technique for AT image or other classification. As described herein, a dictionary learning procedure learns the multi-view class-specific dictionaries simultaneously under a group sparsity constraint, enforcing collaboration of the information from different views in order to generate discriminative latent features (sparse codes) from the training data (e.g., data optimized for a given classification task, such as AT image classification. Performance comparisons with other classifiers (e.g., an SVM classifier, a multi-layer perceptron (MLP) classifier, and a principal component analysis (PCA) deep learning classifier revealed that an example classifier of the disclosed methods and systems achieved better classification accuracy.

The present disclosure has been described with reference to specific examples that are intended to be illustrative only and not to be limiting of the disclosure. Changes, additions and/or deletions may be made to the examples without departing from the spirit and scope of the disclosure.

The foregoing description is given for clearness of understanding only, and no unnecessary limitations should be understood therefrom.

What is claimed is:

1. A computer-implemented method of tissue assessment, the computer-implemented method comprising:

obtaining, with a processor, a plurality of input data samples, each input data sample being representative of tissue in one of multiple views;

determining, with the processor, a set of sparse codes for each input data sample of the plurality of input data samples;

determining, with the processor, a reconstruction error for the set of sparse codes relative to each dictionary of a set of machine-learned composite dictionaries; and providing, with the processor, the tissue assessment in accordance with the machine- learned composite dictionary in the set of machine-learned composite dictionaries having a minimum reconstruction error of the determined reconstruction errors, wherein each machine-learned composite dictionary of the set of machine-learned composite dictionaries comprises a plurality of constituent dictionaries, each constituent dictionary of the plurality of constituent dictionaries being associated with a respective one of the multiple views.

2. The computer-implemented method of claim 1, wherein determining the set of sparse codes comprises implementing, with the processor, an optimization based on each machine-learned composite dictionary of the set of machine-learned composite dictionaries.

3. The computer-implemented method of claim 1, wherein the set of sparse codes are collectively representative of all of the multiple views.

4. The computer-implemented method of claim 1, wherein obtaining the plurality of input data samples comprises acquiring, with a scanner, three-dimensional image data of the tissue.

5. The computer-implemented method of claim 1, wherein:

a first dictionary of the set of machine-learned composite dictionaries is representative of images of abnormal lung tissue; and a second dictionary of the set of machine-learned composite dictionaries is representative of images of healthy lung tissue.

6. The computer-implemented method of claim 1, further comprising implementing, by the processor, an image segmentation procedure on image data.

7. The computer-implemented method of claim 1, wherein the tissue assessment comprises a prediction of therapeutic outcome.

8. The computer-implemented method of claim 2, wherein the optimization comprises a joint $l_{12}$ norm minimization calculation.

9. The computer-implemented method of claim 4, wherein:

the multiple views comprise respective cross-sectional views of the three-dimensional image data; and each constituent dictionary of the plurality of constituent dictionaries is associated with one of the respective cross-sectional views of the three-dimensional input image data.

10. The computer-implemented method of claim 5, wherein:

the images of abnormal lung tissue are indicative of a presence of air-trapping; and the images of healthy lung tissue are indicative of an absence of air-trapping.

11. The computer-implemented method of claim 7, wherein the prediction of therapeutic outcome is indicative of length of hospital stay.

12. A computer-implemented method for building a machine-learned classifier, the computer-implemented method comprising:

obtaining, with a processor, a plurality of training data samples, each training input sample being associated with one of a plurality of classes, and each input data sample being representative of tissue in one of multiple views; and implementing, with the processor, a sparse code-based optimization to build a set of composite dictionaries of the machine-learned classifier based on the plurality of data samples of the training data, each composite dictionary of the plurality of composite dictionaries being representative of one of the plurality of classes, wherein each composite dictionary of the set of composite dictionaries comprises a plurality of constituent dictionaries, each constituent dictionary of the plurality of constituent dictionaries being associated with a respective one of the multiple views.

13. The computer-implemented method of claim 12, wherein implementing the sparse code-based optimization comprises iteratively updating sparse codes for the plurality of training data samples.

14. The computer-implemented method of claim 13, wherein implementing the sparse-code base optimization comprises alternating between iteratively updating dictionary bases of a respective one of the set of composite dictionaries for a given set of the sparse codes and iteratively updating the sparse codes for a given set of the dictionary bases.

15. The computer-implemented method of claim 13, wherein iteratively updating the sparse codes comprises implementing an orthogonal matching pursuit (OMP) procedure.

16. The computer-implemented method of claim 13, wherein implementing the sparse code-based optimization comprises iteratively updating bases of a respective composite dictionary of the set of composite dictionaries in accordance with a minimization problem, the minimization problem comprising:

a first component directed to minimizing differences of the training data samples associated with the class for which the respective composite dictionary is representative; and a second component directed to maximizing differences between the training data samples associated with a different class for which the respective composite dictionary is not representative.

17. The computer-implemented method of claim 16, wherein iteratively updating the bases comprises implementing a block coordinate descent procedure to update the bases one at a time.

18. A system for tissue assessment, the system comprising:

a scanner configured to capture scan data representative of tissue in multiple views;

a memory on which input instructions, sparse code optimization instructions, reconstruction error instructions, and output instructions are stored;

a processor coupled to the memory and configured to execute the input instructions to generate a plurality of input data samples based on the scan data; and a storage device on which a set of machine-learned composite dictionaries is stored;

wherein:

the processor is configured to execute the sparse code optimization instructions to determine a set of sparse codes for each input data sample of the plurality of input data samples;

the processor is configured to execute the reconstruc-
tion error instructions to determine a reconstruction
error for the set of sparse codes relative to each
machine-learned composite dictionary of the set of
machine-learned composite dictionaries;

the processor is configured to execute the output
instructions to provide the tissue assessment in
accordance with the machine-learned composite dic-
tionary in the set of machine- learned composite
dictionaries having a minimum reconstruction error
of the determined reconstruction errors; and each machine-learned composite dictionary of the set
of machine-learned composite dictionaries com-
prises a plurality of constituent dictionaries, each
constituent dictionary of the plurality of constituent
dictionaries being associated with a respective one of
the multiple views.

* * * * *